United States Patent [19]

Hinkle

[11] Patent Number: 4,926,885
[45] Date of Patent: May 22, 1990

[54] METHOD OF SELECTING MEDICATION AND MEDICAL EQUIPMENT

[76] Inventor: Allen J. Hinkle, Box 451, Hardy Hill Rd., Lebanon, N.H. 03766

[21] Appl. No.: 158,548

[22] Filed: Feb. 22, 1988

[51] Int. Cl.$^5$ .................................................. G01B 3/02
[52] U.S. Cl. ....................................................... 128/898
[58] Field of Search ............. 128/897, 898; 33/137 R, 33/511–515, 755, 759, 494; 364/563

[56] References Cited

U.S. PATENT DOCUMENTS

| | | | |
|---|---|---|---|
| 2,809,458 | 10/1987 | Wilbourn | 33/137 R |
| 3,501,849 | 2/1979 | Olsen | 35/6 |
| 4,645,491 | 5/1981 | Evans | 604/158 |
| 4,679,160 | 7/1987 | Whitener | 364/563 |
| 4,713,888 | 12/1987 | Broselon | 33/137 R |

OTHER PUBLICATIONS

Endotracheal Tube Sizes For Children; Philip J. Keep and Margaret L. M. Manford; Anasthesia, vol. 29, pp. 181–185, (1974).

A Pre-Formed Pediatric Orotracheal Tube Design Based on Anatomical Measurements, by G. A. R. Morgan and D. J. Steward, Can. Anaesth. Soc. J. vol. 29, No 1, pp. 9–11, (Jan. 1982).

Estimating Ideal Body Mass In Children; Scott L. Traub and Leslie Kichen, The American Journal of Hospital Pharmacy, 40: pp. 107–110, (1983).

Is There A Correlation Between Vertebral Length and Volume of Local Anasthetic Required to Produce Epidural Anasthesia; Divina J. Santos, Mustague Juneja, Donald D. Denson, Carolyn Nicholson, and Philip O. Bridenbaugh Regional Anesthesia, vol. 13, No. 1, p. 39.

A Rapid and Reliable Method of Selecting Endotracheal Tube Size in Children; Allen J. Hinkle, Anesthesia Analog, 67, 592, (1988).

*Primary Examiner*—Max Hindenburg
*Assistant Examiner*—John P. Lacyk
*Attorney, Agent, or Firm*—Janine J. Weins; Michael J. Weins

[57] ABSTRACT

The present invention is directed to a method of identifying and selecting medical equipment, medication doses and/or medical supplies; and to the equipment used to carry out the method. The present invention measures a specific anatomical dimension: this dimension is correlated to a code which can be a color and/or pattern. The color and/or pattern in turn is used to identify and select medication dosage, medical equipment and/or medical supplies. In one embodiment a linear strip is divided into regions of color and/or pattern. The color and/or pattern associated with the patient's length is used to identify and select medication, medical equipment and/or medical supplies. The equipment, medication and supplies can be group by code, contained in a package bearing the code, or marked by the code. In a preferred embodiment an ultrasonic measuring device is used to determine the code associated with a patient's length. In another preferred embodiment the patient is provided with a coded identification bracelet. In a preferred embodiment a code for length in combination with a particular medical emergency and optionally a medical history are used to select medical equipment, medication and/or medical supplies.

11 Claims, 6 Drawing Sheets

METHOD OF SELECTING MEDICATION AND MEDICAL EQUIPMENT

FIELD OF INVENTION

The present invention is directed to a method of selecting medication dose, medical equipment, and medical supplies; and to the equipment used to carry out the method. The method of the present invention utilizes pattern and/or color to assist in identification and selection. The method and equipment of the present invention reduces the time required to respond to a medical emergency and the likelihood of error in the selection of medication dose, medical equipment and medical supplies.

BACKGROUND ART

The dose of medication and the size of medical equipment must be appropriate if the patient is to receive the best treatment. Since the anatomical dimensions of patients and in particular pediatric patients vary, the appropriate medication dose and medical equipment size may vary from patient to patient and over time for the same patient. The appropriate endotracheal tube diameter will depend on the diameter of the patient's airway.

The appropriate quantity of medication and medical equipment for a particular patient is currently determined by physician judgement and calculation. Once the medication dose and equipment size has been determined the equipment must be selected from a collection of equipment and the medication dose measured. This process has multiple steps, each of which require time, intellect, and attention. During each step in the process there is the possibility that errors will be introduced. The errors can cause a delay in treatment, and/or diminish the effectiveness of the treatment.

Endotrachael tubes having as many as ten different diameters may be used to secure the airway of pediatric patients. Since the need to secure the airway may arise in a medical emergency the time required to identify the appropriate endotracheal tube and then select the appropriate tube from a collection of endotracheal tubes may be costly to the treatment process; and in certain critical situations the patient may be at great risk during the time they are awaiting treatment.

Patient weight is frequently correlated to medication dose and equipment size by use of a table, graph or formula. This process is time consuming, thus valuable time may be lost. In certain situations it may be difficult to weigh the patient or equipment for determining the weight may not be available.

Recent research has indicated that, particularly for pediatric patients, weight may not be the best predictor of the appropriate equipment size and medication dose. For example a publication by Scott L. Traub and Leslie Kichen; ESTIMATING IDEAL BODY MASS IN CHILDREN; The American Journal of Hospital Pharmacy; 40: pages 107–10; 1983 analyzed data from over 20,000 children and concluded that height was a better predictor of medication dose requirements than was body weight. An abstract by Allen J. Hinkle; A RAPID AND RELIABLE METHOD OF SELECTING ENDOTRACHAEL TUBE SIZES IN CHILDREN; Anesthesia Analog Journal; 1988 showed a high correlation between endotracheal tube size and body length. An article by Divina J. Santos, Mustaque Juneja, Donald D. Denson, Carolyn Nicholson and Phillip Bridenbaugh; IS THERE A CORRELATION BETWEEN VERTEBRAL LENGTH AND VOLUME OF LOCAL ANESTHETIC REQUIRED TO PRODUCE EPIDURAL ANESTHESIA, Regional Anesthesia, Vol. 13, No. 1, page 39 shows a correlation of spinal length to appropriate dosage of medication. An article by Philip J. Keep and Margaret M. Manford; ENDOTRACHEAL TUBE SIZES FOR CHILDREN; Volume 29; Anasthesia; pages 181–185; 1974 concluded that for determining the correct endotracheal tube size "estimates based on height are more accurate as a calculator than either age or weight".

There exists a need for a method of quickly and accurately selecting medication dose, medical equipment, and medical supplies such that the type, quantity and size are appropriate for the patient and the situation. The present invention is directed to such a method and to the associate equipment for carrying out the method so as to quickly, accurately, and reproducibly assisting a practitioner in selecting the type, quantity and size of medication, medical equipment and/or medical supplies.

SUMMARY OF THE INVENTION

It is an object of the present invention to provide a method of selecting the size of medical equipment appropriate for the patient and the situation.

It is an object of the present invention to provide a method which reduces the chance of error in the selection of medical equipment.

It is an object of the present invention to provide a reliable method of selecting the dosage of medication appropriate for the patient.

It is an object of the present invention to provide a method of selecting medications which reduces the response time for treating pediatric patients in an emergency situation.

It is an object of the present invention to provide a method of selecting the size of medical equipment so as to reduce the response time for treatment of a pediatric patient in an emergency medical situation.

It is an object of the present invention to provide a method of selecting the appropriate dose of medication for pediatric patients ranging in age from new born to sixteen years.

It is an object of the present invention to reduce the error in selecting equipment for patients and in particular pediatric patients.

It is an object of the present invention to improve the speed with which medication can be selected and thereby to increase the likelihood of a successful outcome in an emergency medical situation.

It is an object of the present invention to provide a method of selecting equipment that may be needed in emergency medical situations so as to reduce the likelihood of error and to reduce the time required for the selection of equipment and thus to improve the probability of a particular medical procedure saving the life of the patient.

It is an object of the present invention to provide a method of selection which excludes the selection of medication that could be detrimental to the patient.

It is an object of the present invention to provide a method of selecting equipment which is appropriate for the particular medical emergency.

It is an object of the present invention to provide a system which will provide a medical practitioner with all of the equipment needed for a particular procedure in response to a single selection process.

These and other objects of the present invention will become apparent from the following figures, descriptions, and preferred embodiments.

The present invention is directed to a method of selection and the equipment used to implement the method. The present invention in its simplest form correlates a specific anatomical dimension to a particular color and/or pattern. The color and/or pattern is used to identify and select medication dosage, medical equipment and/or medical supplies.

The present invention correlates an anatomical dimension of a patient to a particular color and/or pattern.

The present invention uses colors and/or patterns to identify equipment of different size.

The present invention utilizes color and/or pattern to identify and distinguish different doses of medication.

The present invention correlates a particular anatomical dimension such as body height to particular medication doses and equipment sizes.

The present invention in its simplest form correlates an anatomical dimension of a particular patient to a color and/or pattern. The color and/or pattern is used to identify and select appropriate medication dosage and equipment size.

In its simplest form the present invention is directed to a strip which is segmented into regions of different color and/or pattern. The patient is measured using the strip. The colors and/or patterns corresponding to the height of the patient is used to select the appropriate medication dose and medical equipment size.

In a preferred embodiment of the present invention an ultrasonic measuring device is used to determine height. The height is correlated to a particular color and/or pattern, by indication of such color and/or pattern on a meter incorporated in the ultrasonic measuring device. The ultrasonic measuring device can be either hand held or may be mounted on an examining table.

To speed the identification process and reduce the likelihood of error, specific sizes of medical equipment, specific doses of medication and quantities of medical supplies are either marked with, grouped by, or dispensed by color and/or pattern. By matching the color and/or pattern associated with the height of the patient to the color and/or pattern associated with the different equipment, medication and/or supplies the appropriate medication, medical equipment and/or medical supplies can be selected and assembled.

In a preferred embodiment of the present invention packets of medication, medical equipment and medical supplies are marked by color and/or pattern. By selecting packets of medication and medical equipment bearing the particular color and/or pattern the practitioner is able to select the appropriate medication and equipment.

In a preferred embodiment of the present invention drawers or shelves containing equipment of a particular size, prepackaged medication doses and/or medical supplies are marked by color and/or pattern.

In an embodiment of the present invention the medical equipment is marked by color and/or pattern.

In a preferred embodiment of the present invention the particular medical emergency in combination with the color and/or pattern associated with a particular patient's anatomical dimensions are input to a dispensing system which then selects, and dispenses medical equipment, medical supplies and/or medications.

In a preferred embodiment of the present invention an ultrasonic measuring device generates a signal in the form of a digital pattern. The signal can be fed directly into a medical dispensing system.

In yet another preferred embodiment an automated dispensing system having keyboard input means is used to dispense medication and medical equipment appropriate for the patient. The color and/or pattern associated with the patient's anatomical dimensions in combination with a color and/or pattern associated with a particular medical emergency, and optionally with the medical background of the patient are input using the keyboard. The dispensing system through the appropriate hardware and software dispenses medication, medical equipment and medical supplies appropriate for treating the patient.

In yet another preferred embodiment of the present invention the patient is provided with an identification bracelet which is coded by a particular color and/or pattern. The bracelet may be coded with a bar code pattern. A bar code reader can be used to read the bar code pattern and input a dispensing system which then automatically selects the appropriate medical equipment, medication and medical supplies.

BEST MODE OF CARRYING THE INVENTION INTO PRACTICE

Figure 1:
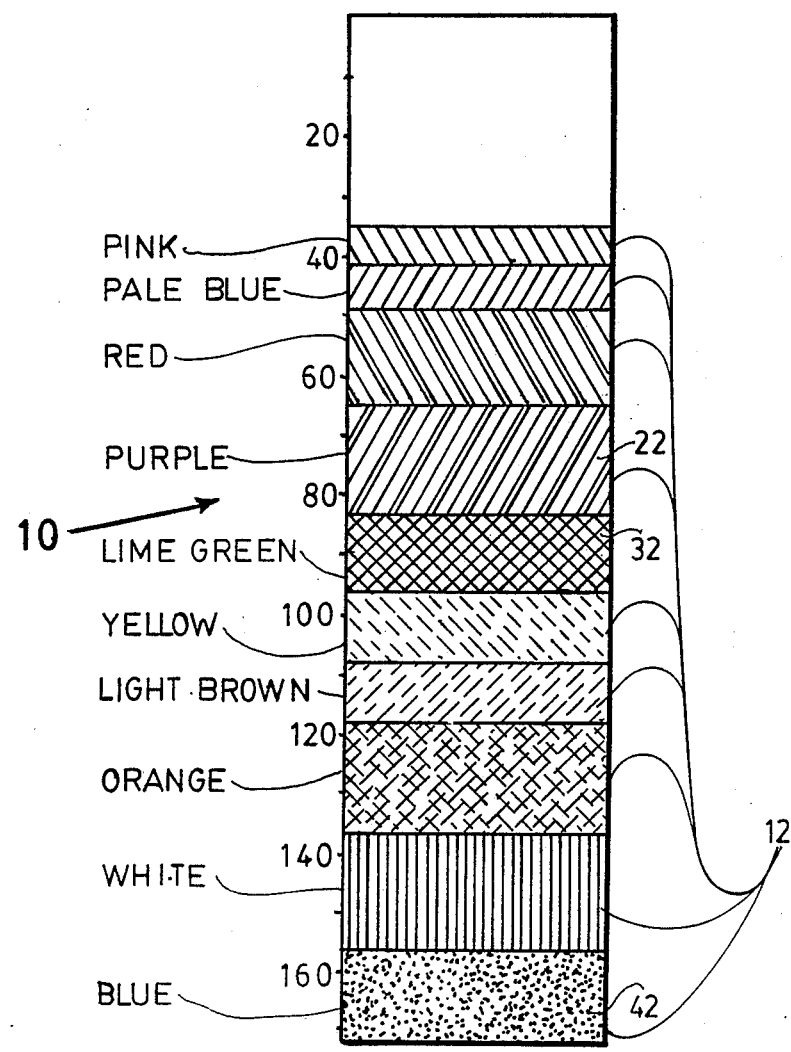
FIG. 1 is a schematic representation of one embodiment of the present invention and shows a linear strip incremented by color and pattern.

FIG. 1 is a representation of a strip 10 for use in determining the pattern and/or color which corresponds to a particular patient's body length. The strip 10 is divided into regions 12 of different color and pattern.

Figure 2:
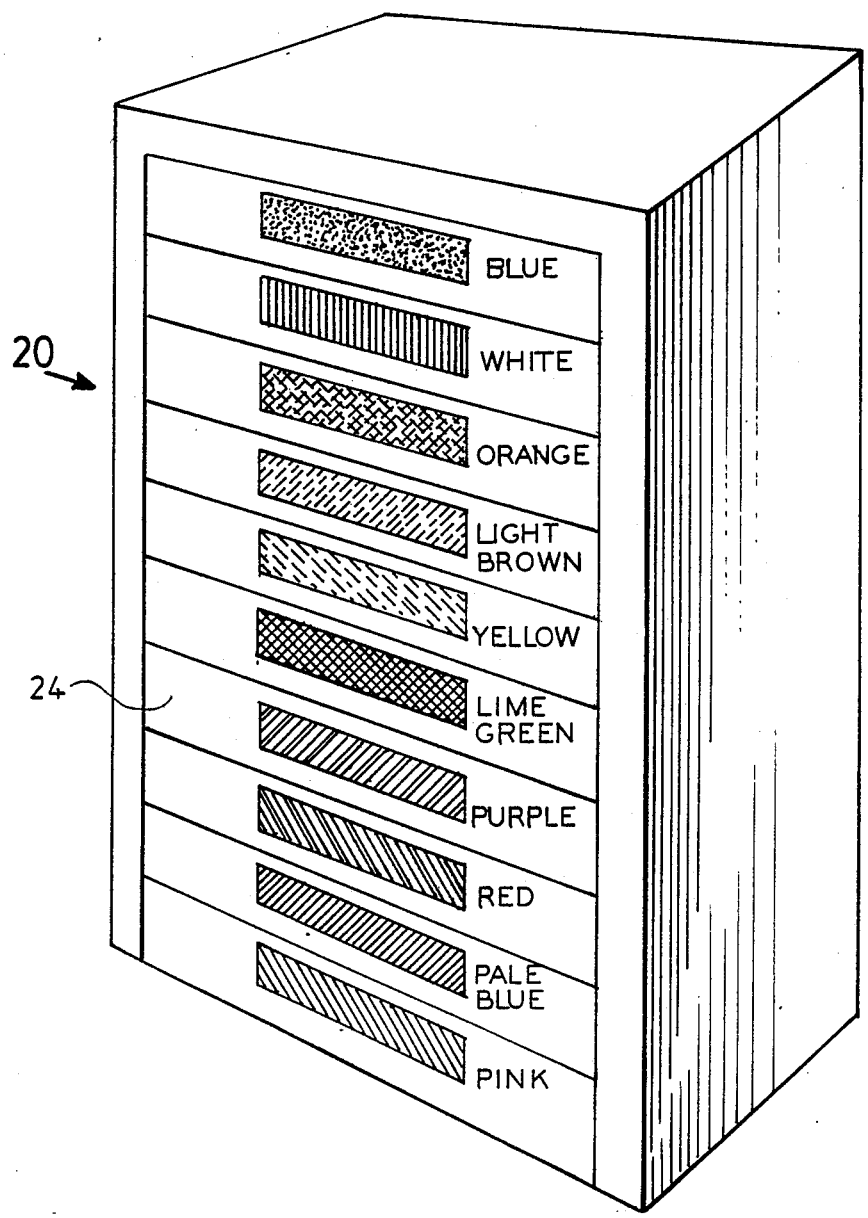
FIG. 2 is a schematic representation of a storage system for use in combination with the linear strip of FIG. 1.
Figure 3:
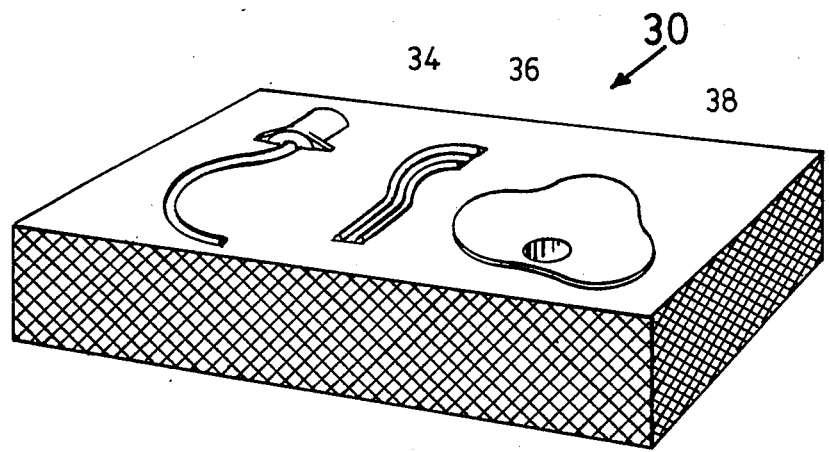
FIG. 3 is a schematic representation of a package of equipment which has been marked with a color and pattern for use with the strip shown in FIG. 1.

FIG. 2 shows a series of drawers 20 which are marked in accordance with the color and pattern increments shown in FIG. 1. For example if a patient were 80 cm long the pattern and/or color associated with their height would be the variably spaced apart negatively sloped lines and the color purple as shown for increment 22 in FIG. 1. The drawer 24 would contain an endotracheal tube 34 of 4.0 mm, an oral airway 36 of 60 mm and a face mask 38 of child size 2. These elements are illustrated in FIG. 3. This equipment would be appropriate for treating a patient 80 cm long. Other equipment such as surgical gloves which would not vary with patient size could also be included in the drawer.

In place of drawers 20, pre-marked packets of equipment and medication can be selected. FIG. 3 shows a packet 30 marked by the cross hatch pattern and the color lime green. This packet would be appropriate for treating a 90 cm long patient who would be indicated in FIG. 1 by increment 32. The packet 30 would contain an endotracheal tube 34 of 4.5 mm, an oral airway 36 of 70 mm and a face mask 38 of child size 2.

Optionally individual items and equipment can be marked and coded in accordance with the pattern or color associated with a particular color or pattern.

Figure 4:
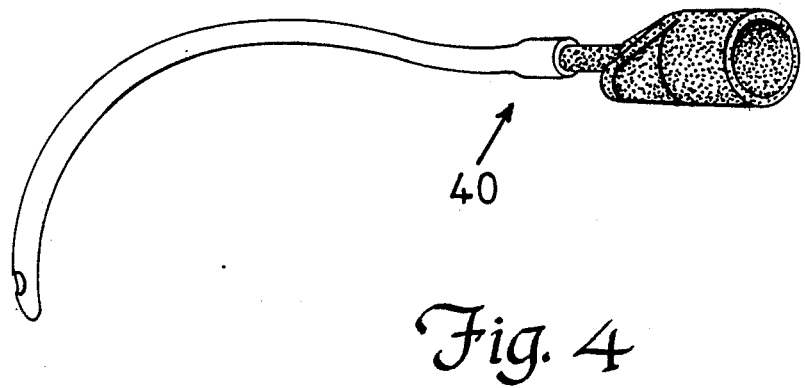
FIG. 4 is a schematic representation of an endotracheal tube which is provided with a patterned colored adaptor to identify the particular tube size. The endotracheal tube, as marked in FIG. 4, can be used in combination with the linear strip shown in FIG. 1.

FIG. 4 shows an endotracheal tube 40 that is marked with a dot pattern and the color blue that would correlate to the increment 42 on FIG. 1. The endotracheal tube is 7.0 mm in diameter and thus would be appropriate for securing the airway of a patient who was 160 cm long.

The pattern and/or color must be clearly distinguishable and readily recognizable.

Preferably the drawers and/or prepackaged equipment should be systematically arranged with the progression consistent with the progression of patient length and thus be arranged as for example the colors and/or patterns are arranged on the strip 10 shown in FIG. 1.

Figure 5:
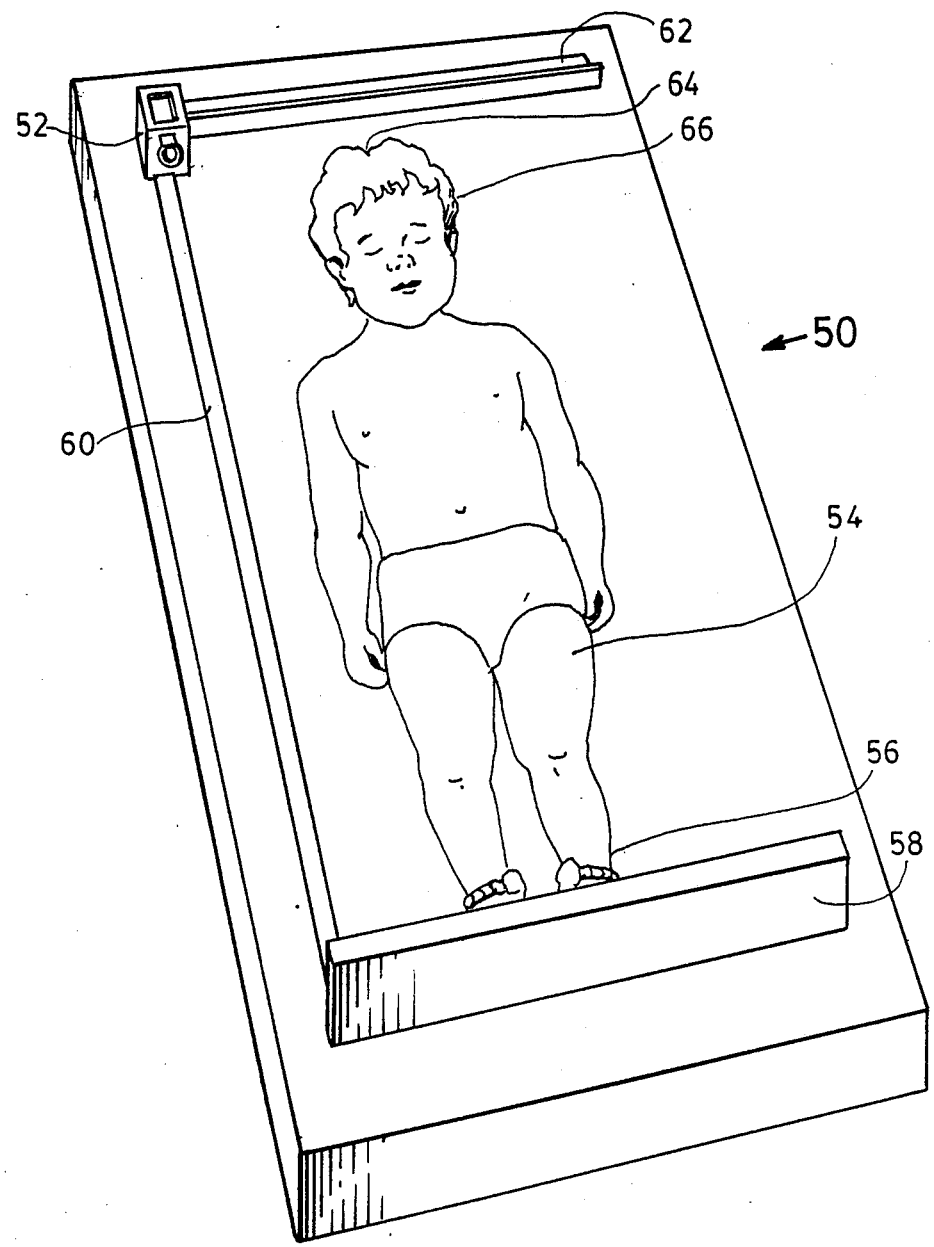
FIG. 5 is a schematic representation of an embodiment of the present invention wherein a track mounted ultrasonic measuring device is used to determine a color and/or pattern which correlates to a patient's length.

FIG. 5 is a schematic representation of a preferred embodiment of the present invention wherein an examining table 50 is provided with a track mounted ultrasonic measuring device 52. A patient 54 is positioned on the table 50 so that their feet 56 are in contact with a foot plate 58. A track 60 is provided to the side 62 of the table 50. The ultrasonic measuring device 52 is slidably mounted on the track 60. Preferably the ultrasonic measuring device 52 is provided with an extension arm 62 to determine the code appropriate for the patient. The ultrasonic measuring device 52 is caused to travel down the track 60 until such time as an extension arm 62 contacts the crown 64 of the head 66 of the patient 52. When the extension arm 62 contacts the crown 64 the ultrasonic device 52 sends a signal to the foot plate 58 which is used to determine the length of the patient. The ultrasonic measuring device 52 translates the length to a color and/or pattern.

Figure 6:
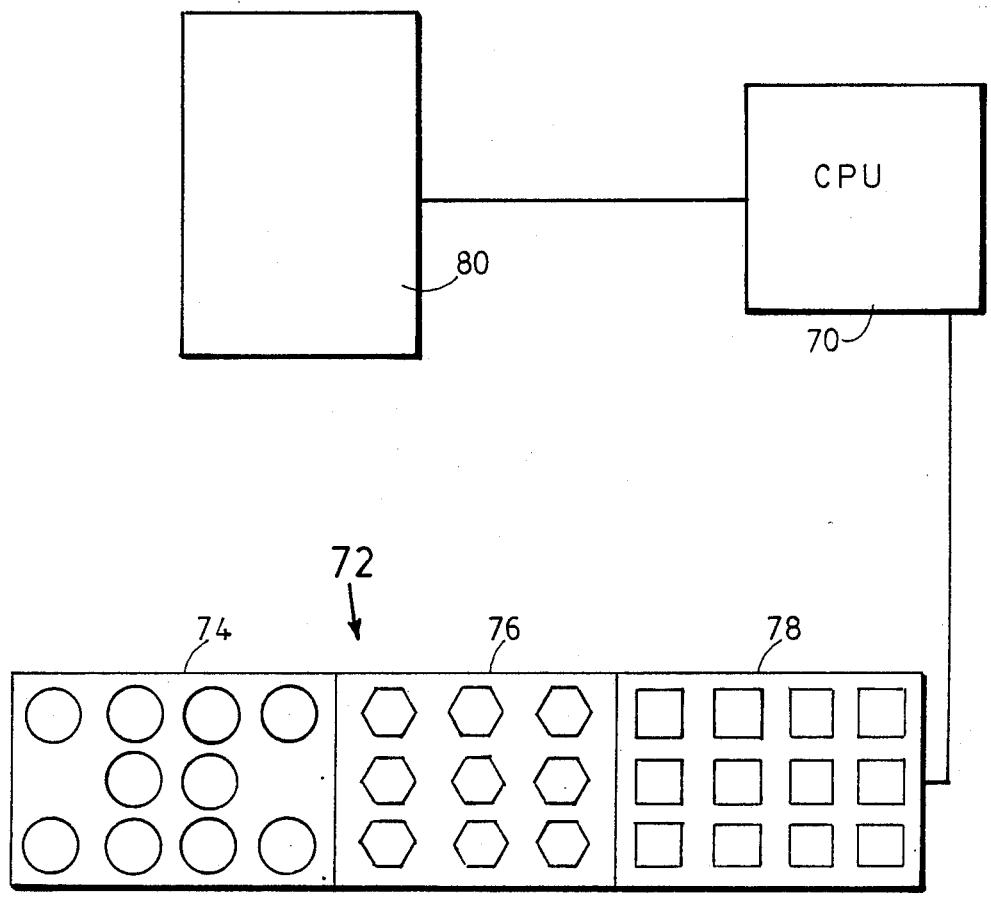
FIG. 6 is an automated dispensing system in accordance with the present invention which allows a color and/or pattern associated with the particular patient's length; a code associating with the particular medical emergency; and a code associated with the patient's medical history to be input into the automatic dispenser system.

Optionally the ultrasonic measuring device can be provided with a digital read out means which will send a signal to a computer processor such as the CPU 70 shown in FIG. 6. The CPU 70 utilizes the appropriate software to select medication dose and medical equipment appropriate for the patient. Optionally, the computer processor system shown in FIG. 6 can be activated through a key pad 72 which is provided with three regions. The first region of the key pad 74 allows for the operator to input a color or pattern which correlates to the height, or other anatomical dimension, of the patient. The second region 76 allows the operator to input the particular medical emergency such as drowning, cardiac arrest or shock. The third optional region 78 allows for the operator to input a medical history of the patient such as diabetic, epileptic or pregnant. Using this automated system it is possible to select medical supplies, medication dose and medical equipment appropriate for the patient and the particular medical emergency which is consistent with the medical history and condition of the patient. The medication, medical equipment and medical supplies are dispensed by the dispensing unit 80.

Figure 7:
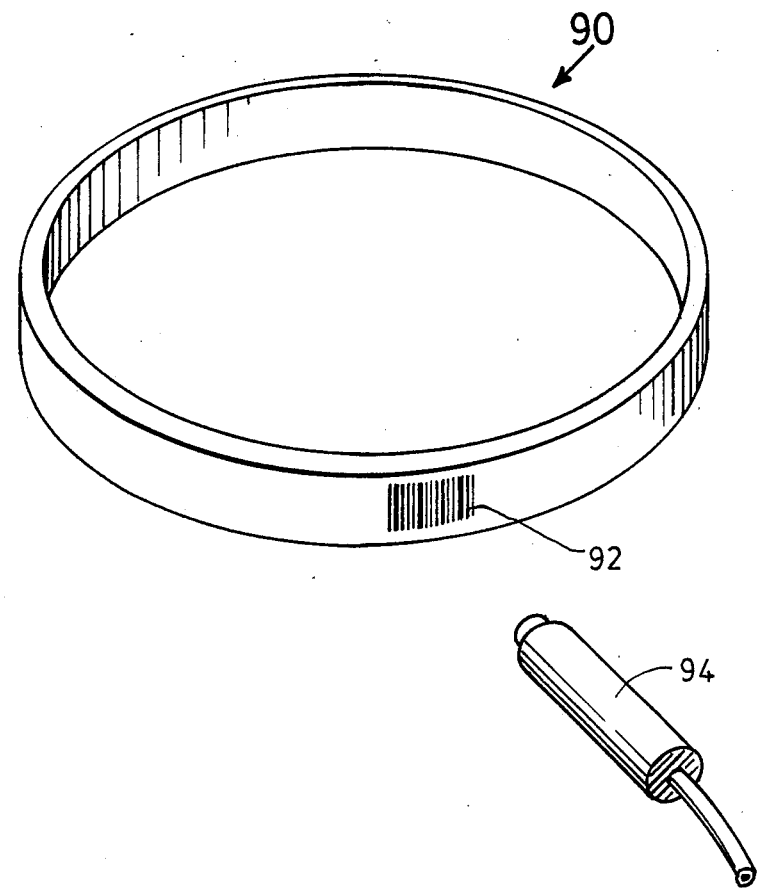
FIG. 7 is a schematic representation of an embodiment of the present invention wherein a colored bar coded patient bracelet is used in combination with a bar code reader.

FIG. 7 shows yet another preferred embodiment of the present invention wherein the patient is provided with an identification bracelet 90. Preferably the identification bracelet 90 is coded by color or pattern so that the color associated with the length of the particular patient can be readily ascertained. In a medical emergency, such as a code blue, the first person on the scene would be able to view the color and thus identify, for example, the endotracheal tube size that would be needed to secure the airway of the patient and could proceed to quickly begin treatment of the patient.

The bracelet 90 can additionally bear a pattern such as a bar coded pattern 92 which contains information such as the patient's history. A bar code reader 94 could be used to input a system such as shown in FIG. 7.

While the invention has been described in terms of preferred embodiments, special configurations, and particular methods it should be appreciated of one skilled in the art that variation in the methods and the equipment can be made by one skilled in the art without departing from the spirit of the invention.

What I claim is:

1. A method for selecting medication and medical equipment for a patient comprising the steps of:
   preparing series of packages based on anatomical dimensions, each of said packages containing a group of elements which correlated to an anatomical dimension;
   coding said packages to correlate with said anatomical dimension;
   determining said anatomical dimension of a patient;
   correlating said anatomical dimension of said patient to said code; and
   selecting from said packages a package with said correlated code.

2. The method of claim 1 wherein said code is color based.

3. The method of claim 1 wherein said code is pattern based.

4. The method of claim 2 wherein said group of elements comprises medications and medical equipment.

5. The method of claim 4 wherein said medical equipment comprises:
   an endotracheal tube;
   an oral airway; and
   a facemask.

6. The method of claim 3 wherein said group of elements comprises medications and medical equipment.

7. The method of claim 22 wherein said medical equipment comprises:
   an endotracheal tube;
   an oral airway; and
   a facemask.

8. The method of claim 2 wherein each of said elements in said packages are color coded.

9. The method of claim 3 wherein each of said elements in said packages are pattern coded.

10. The method of claim 4 wherein said package is a drawer.

11. The method of claim 6 wherein said package is a drawer.

* * * * *